(12) United States Patent
Oyler et al.

(10) Patent No.: US 9,732,376 B2
(45) Date of Patent: Aug. 15, 2017

(54) SAMPLE COLLECTION DEVICE

(71) Applicant: Ancestry.com DNA, LLC, Provo, UT (US)

(72) Inventors: Benjamin J. Oyler, Cedar Hills, UT (US); Kenneth G. Chahine, Park City, UT (US); Catherine Ann Ball, Mountain View, CA (US); Federico C. A. Gaeta, Mountain View, CA (US)

(73) Assignee: ANCESTRY.COM DNA, LLC., Lehi, UT (US)

( * ) Notice: Subject to any disclaimer, the term of this patent is extended or adjusted under 35 U.S.C. 154(b) by 247 days.

(21) Appl. No.: 14/448,721

(22) Filed: Jul. 31, 2014

(65) Prior Publication Data

US 2015/0056716 A1    Feb. 26, 2015

Related U.S. Application Data (60) Provisional application No. 61/861,329, filed on Aug. 1, 2013.

(51) Int. Cl.
*B01L 3/14*    (2006.01)
*C12Q 1/68*    (2006.01)
*A61B 10/00*    (2006.01)

(52) U.S. Cl.
CPC ........ *C12Q 1/6806* (2013.01); *A61B 10/0051* (2013.01); *A61B 10/0096* (2013.01); *Y10T 436/2525* (2015.01)

(58) Field of Classification Search
CPC ............ A61B 10/0051; A61B 10/0096; Y10T 436/2525; C12Q 1/6806; B01L 2300/0672; B01L 2300/044; B01L 2400/0683

See application file for complete search history.

(56) References Cited

U.S. PATENT DOCUMENTS

| | | |
|---|---|---|
| 3,831,742 A | 8/1974 | Gardella et al. |
| 4,131,016 A | 12/1978 | Layton |
| 4,217,798 A | 8/1980 | McCarthy et al. |
| 4,301,812 A | 11/1981 | Layton et al. |
| 4,982,553 A | 1/1991 | Itoh |
| 5,283,038 A | 2/1994 | Seymour |

(Continued)

FOREIGN PATENT DOCUMENTS

| | | |
|---|---|---|
| CN | 202355427 | 8/2012 |
| CN | 202355427 U | 8/2012 |

(Continued)

OTHER PUBLICATIONS

New Zealand Examination Report, New Zealand Application No. 629537, May 12, 2016, 2 pages.

(Continued)

*Primary Examiner* — Christopher A Hixson
(74) *Attorney, Agent, or Firm* — Fenwick & West LLP (57) ABSTRACT

A sample collection device having a sample tube, funnel, and cap having a capsule and a piercing insert, the capsule having a stabilization solution. After depositing the sample into the tube via the funnel, the cap is screwed onto the tube, piercing the capsule and releasing the stabilization fluid into the tube. The device can be used at home without clinicial supervision for collecting a saliva sample and transporting the sample to an analysis location for DNA analysis.

15 Claims, 9 Drawing Sheets

(56) References Cited

U.S. PATENT DOCUMENTS

| | | | |
|---|---|---|---|
| 5,396,986 | A | 3/1995 | Fountain et al. |
| 5,736,355 | A | 4/1998 | Dyke et al. |
| 5,927,549 | A | 7/1999 | Wood |
| 5,933,498 | A | 8/1999 | Schneck et al. |
| 6,003,728 | A | 12/1999 | Elliott |
| 6,152,296 | A | 11/2000 | Shih |
| 6,228,323 | B1 | 5/2001 | Asgharian et al. |
| 6,543,612 | B2 | 4/2003 | Lee et al. |
| 6,627,152 | B1 | 9/2003 | Wong |
| 6,786,330 | B2 | 9/2004 | Mollstam et al. |
| 7,055,685 | B1 | 6/2006 | Patterson et al. |
| 7,178,683 | B2 | 2/2007 | Birkmayer et al. |
| 7,482,116 | B2 | 1/2009 | Birnboim |
| 7,537,132 | B2 | 5/2009 | Marple et al. |
| 7,645,424 | B2 | 1/2010 | O'Donovan |
| 8,221,381 | B2 | 7/2012 | Muir et al. |
| 9,207,164 | B2 | 12/2015 | Muir et al. |
| 2003/0089627 | A1* | 5/2003 | Chelles ............ B65D 51/2821 206/219 |
| 2004/0132091 | A1 | 7/2004 | Ramsey et al. |
| 2006/0201948 | A1 | 9/2006 | Ellson et al. |
| 2007/0170142 | A1 | 7/2007 | Cho |
| 2009/0216213 | A1 | 8/2009 | Muir et al. |
| 2010/0099149 | A1 | 4/2010 | Birnboim et al. |
| 2010/0258457 | A1* | 10/2010 | Seelhofer .......... B65D 51/2821 206/222 |
| 2011/0207621 | A1* | 8/2011 | Montagu .......... B01L 3/502784 506/9 |
| 2011/0212002 | A1 | 9/2011 | Curry et al. |
| 2012/0046574 | A1 | 2/2012 | Skakoon |
| 2012/0061392 | A1 | 3/2012 | Beach et al. |
| 2013/0092690 | A1 | 4/2013 | Skakoon |
| 2013/0164738 | A1* | 6/2013 | Becker ................. B01L 3/502 435/6.1 |

FOREIGN PATENT DOCUMENTS

| | | |
|---|---|---|
| DE | 199 50 884.4 A1 | 4/2001 |
| DE | 199 50 884 A1 | 4/2001 |
| EP | 0 133 461 A2 | 2/1985 |
| EP | 0273015 A2 | 6/1988 |
| JP | 6-78282 U | 11/1994 |
| JP | 9 255047 A2 | 9/1997 |
| JP | H09-255047 | 9/1997 |
| JP | 11-227774 | 8/1999 |
| WO | WO 98/03265 A1 | 1/1998 |
| WO | WO 03/104251 A2 | 12/2003 |
| WO | WO 2005/023667 A1 | 3/2005 |
| WO | WO 2005/044670 A1 | 5/2005 |
| WO | WO 2005/049207 A1 | 6/2005 |
| WO | WO 2007/068094 A1 | 6/2007 |
| WO | WO-2015/017701 A1 | 2/2015 |

OTHER PUBLICATIONS

Taiwan Office Action, Taiwan Application No. 103126477, Apr. 29, 2016, 5 pages.

Taiwan Office Action, Taiwan Application No. 103126477, Aug. 26, 2015 (with English Search Report), 6 pages.

International Search Report and Written Opinion for PCT International Application No. PCT/US2014/049236, Nov. 14, 2014, 14 pages.

Biomek® FX: User's Manual, Beckman Coulter, May 2000, 5 pages.

Declaration of John M. Collins, Ph.D. In Support of Plaintiff's Reply in Support of Motion for Preliminary Injunction, *DNA Genotek Inc. v. Spectrum Solutions L.L.C., and Spectrum DNA,* Case No. 3:16-cv-01544-JLS-NLS, Aug. 19, 2016, 65 pages.

Deposition of: John Collins, Ph.D., *DNA Genotek Inc. v. Spectrum DNA , Spectrum Solutions L.L.C., and Spectrum Packaging L.L.C.,* C.A. No. 15-CV-00661-SLR, Nov. 13, 2015, 5 pages.

Deposition of John M. Collins, Ph.D., *Ancestry.com DNA, LLC v. DNA Genotek Inc., Inter Partes* Review No. IPR2016-00060, U.S. Pat. No. 8,221,381, Aug. 24, 2016, 99 pages.

Slip Sheet :Exhibit 1023 Not Filed Previously Submitted as Paper 19, Institution Decision from the Patent Trial and Appeal Board (Paper 19), 1 page.

Slip Sheet : Exhibit 1022 Not Filed Herewith Previously Submitted as Paper 5, Resubmitted Petition for Inter Partes Review for U.S. Pat. No. 8,221,381 (Paper 5), 1 page.

Declaration of Melanie L. Mayer in Support of Petitioner's Motion for Pro Hac Vice Admission of Melanie L. Mayer Pursuant to 37 C.F.R. § 42.10(c), *Ancestry.com DNA, LLC v. DNA Genotek Inc., Inter Partes* Review No. IPR2016-00060, U.S. Pat. No. 8,221,381 B2, Feb. 2, 2016, 5 pages.

Declaration of Michael J. Sacksteder in Support of Petitioner's Motion for Pro Hac Vice Admission of Michael J. Sacksteder Pursuant to 37 C.F.R. § 42.10(c), *Ancestry.com DNA, LLC v. DNA Genotek Inc., Inter Partes* Review No. IPR2016-00060, U.S. Pat. No. 8,221,381 B2, Feb. 2, 2016, 5 pages.

Claim Element Chart, '381 Patent, undated, 4 pages.

U.S. Appl. No. 60/523,104, Nov. 19, 2003, 9 pages.

Declaration of Terry Layton, Ph.D. in Support of Defendants' Opposition to DNA Genotek's Motion for Preliminary Injunction, *DNA Genotek Inc. v. Spectrum DNA , Spectrum Solutions L.L.C., and Spectrum Packaging L.L.C.,* C.A. No. 15-CV-00661-SLR, Oct. 2, 2015, 38 pages.

Defendants' Brief in Opposition to DNA Genotek's Motion for Preliminary Injunction, *DNA Genotek Inc. v. Spectrum DNA , Spectrum Solutions L.L.C., and Spectrum Packaging L.L.C.,* C.A. No. 15-CV-00661-SLR, Oct. 9, 2015, 37 pages.

"The American Heritage® Dictionary of the English Language," Fourth Edition, Houghton Mifflin Company, 2000, p. 318, p. 643, p. 896, p. 1355, p. 1483, p. 1915.

Declaration of Juan C. Lasheras, Ph.D., *DNA Genotek Inc. v. Spectrum DNA , Spectrum Solutions L.L.C., and Spectrum Packaging L.L.C.,* C.A. No. 15-CV-00661-SLR, Aug. 24, 2015, 154 pages.

Plaintiff DNA Genotek Inc.'s Opening Brief in Support of Motion for Preliminary Injunction, *DNA Genotek Inc. v. Spectrum DNA , Spectrum Solutions L.L.C., and Spectrum Packaging L.L.C.,* C.A. No. 15-CV-00661-SLR, Aug. 24, 2015, 26 pages.

Terry N. Layton, Ph.D. Curriculum Vitae, 4 pages.

Declaration of Terry N. Layton, Ph.D., Ancestry.com DNA, LLC, Inter Partes Review, U.S. Pat. No. 8,221,381, Oct. 20, 2015, 130 pages.

File History of U.S. Pat. No. 8,221,381, Filed Jun. 9, 2008, 401 pages.

Declaration of John R. Lanham in Support of Motion for Pro Hac Vice Admission of John R. Lanham Under 37 C.F.R. § 42.10(c), *Ancestry.com DNA, LLC v. DNA Genotek Inc.,* U.S. Pat. No. 8,221,381, *Inter Partes* Review No. IPR2016-00060, Aug. 11, 2016, 4 pages.

ASTM International: Standard Test Method for Static and Kinetic Coefficients of Friction of Plastic Film and Sheeting, undated, 6 pages.

Declaration of Terry N. Layton, Ph.D., Ancestry.com DNA, LLC, Inter Partes Review of U.S. Pat. No. 8,221,381, Jun. 3, 2016, 96 pages.

Petition for *Inter Partes* Review of U.S. Pat. No. 8,221,381, *Ancestry.com DNA, LLC v. DNA Genotek Inc.,* Jun. 3, 2016, 86 pages.

John M. Collins, Ph.D. Curriculum Vitae, 4 pages.

Declaration of John M. Collins, Ph.D., *Ancestry.com DNA, LLC v. DNA Genotek, Inc.,* U.S. Pat. No. 8,221,381, *Inter Partes* Review No. IPR2016-00060, Jun. 22, 2016, pages.

Deposition of Terry Layton, Ph.D., *Ancestry.com DNA, LLC v. DNA Genotek Inc.,* U.S. Pat. No. 8,221,381, *Inter Partes* Review No. 2016-00060, May 25, 2016, 172 pages.

Department of Commerce, United States Patent and Trademark Office, Changes to Implement Miscellaneous Post Patent Provisions of the Leahy-Smith America Invents Act, Dec. 29, 2015, 39 pages.

Patent Technology Centers Management, USPTO, undated, 57 pages, [Online] [Retrieved on Feb. 3, 2016].

Screenshot of Patent Application Information Retrieval, U.S. Appl. No. 09/186,615, 2 pages.

(56) References Cited

OTHER PUBLICATIONS

Defendants' Brief in Opposition to DNA Genotek's Motion for Preliminary Injunction, *DNA Genotek Inc.* v. *Spectrum DNA, Spectrum Solutions L.L.C.* and *Spectrum Packaging L.L.C.*, C.A. No. 15-661-SLR, Oct. 9, 2015, 37 pages.
Record of Oral Hearing, *Ancestry.com DNA, LLC* vs. *DNA Genotek Inc.*, Case IPR2016-00060, Paper No. 35, Jan. 12, 2017, 54 pages.
Petitioner's Mandatory Change-Of-Information Notices Under 37 C.F.R. § 42.8(a)(3), *Ancestry.com DNA, LLC* v. *DNA Genotek Inc.*, Case IPR2016-00060, Dec. 5, 2016, 6 pages.
Order, Request for Oral Hearing, 37 C.F.R. § 42.70, *Ancestry.com DNA, LLC* v. *DNA Genotek Inc.*, Case IPR2016-00060, Nov. 2, 2016, 4 pages.
Patent Owner's Request for Oral Argument, *Ancestry.com DNA, LLC* v. *DNA Genotek Inc., Inter Partes* Review No. IPR2016-00060, Oct. 26, 2016, 4 pages.
Petitioner Ancestry.com DNA LLC's Request for Oral Argument Pursuant to 37 C.F.R. § 42.70(a), *Ancestry.com DNA, LLC* v. *DNA Genotek Inc.*, Case IPR 2016-00060, Sep. 20, 2016, 4 pages.
Petitioner Ancestry.com DNA, LLC's Updated Exhibit List, *Ancestry.com DNA, LLC* v. *DNA Genotek Inc.*, Case IPR 2016-00060, Sep. 6, 2016, 5 pages.
Petitioner Ancestry.com DNA, LLC's Reply to Patent Owner's Response, *Ancestry.com DNA, LLC* v. *DNA Genotek Inc.*, Case IPR 2016-00060, Sep. 6, 2016, 40 pages.
Order Granting Motion for Pro Hac Vice Admission of John R. Lanham, 37 C.F.R § 42.10, *Ancestry.com DNA, LLC* v. *DNA Genotek Inc.*, Case IPR 2016-00060, Aug. 19, 2016, 3 pages.
Patent Owner's Motion for Pro Hac Vice Admission of John R. Lanham, 37 C.F.R § 42.10(c), *Ancestry.com DNA, LLC* v. *DNA Genotek Inc., Inter Partes* Review No. IPR2016-00060, Aug. 11, 2016, 7 pages.
Petitioner's Notice of Deposition of John M. Collins, Ph.D., *Ancestry.com DNA, LLC* v. *DNA Genotek Inc., Inter Partes* Review No. IPR2016-00060, Aug. 2, 2016, 3 pages.
Patent Owner's Updated Mandatory Notices, *Ancestry.com DNA, LLC* v. *DNA Genotek Inc., Inter Partes* Review No. IPR2016-00060, Jun. 23, 2016, 5 pages.
Patent Owner's Response, *Ancestry.com DNA, LLC* v. *DNA Genotek Inc., Inter Partes* Review No. IPR2016-00060, Jun. 22, 2016, 28 pages.
Deposition Notice of Terry N. Layton, Ph.D., *Ancestry.com DNA, LLC* v. *DNA Genotek Inc., Inter Partes* Review No. IPR2016-00060, May 11, 2016, 3 pages.
Scheduling Order, *Ancestry.com DNA, LLC* v. *DNA Genotek Inc.*, Case IPR2016-00060, Apr. 8, 2016, 7 pages.
Decision Institution of Inter Partes Review 37 C.F.R. § 42.108, *Ancestry.com DNA, LLC* v. *DNA Genotek Inc.*, Case IPR2016-00060, Apr. 8, 2016, 23 pages.
Order Decision Granting Motion for Pro Hac Vice Admission of Michael J. Sacksteder 37 C.F.R. § 42.10, *Ancestry.com DNA, LLC* v. *DNA Genotek Inc.*, Case IPR2016-00060, Feb. 25, 2016, 3 pages.
Order Decision Granting Motion for Pro Hac Vice Admission of Melanie L. Mayer 37 C.F.R. § 42.10, *Ancestry.com DNA, LLC* v. *DNA Genotek Inc.*, Case IPR2016-00060, Feb. 25, 2016, 3 pages.
Patent Owner's Preliminary Response, *Ancestry.com DNA, LLC* v. *DNA Genotek Inc., Inter Partes* Review No. IPR2016-00060, Feb. 3, 2016, 51 pages.
Exhibit List, *Ancestry.com DNA, LLC* v. *DNA Genotek Inc., Inter Partes* Review No. IPR2016-00060, Feb. 2, 2016, 4 pages.
Petitioner Ancestry.com DNA, LLC's Motion for Pro Hac Vice Admission of Michael J. Sacksteder Pursuant to 37 C.F.R. § 42.10(c), *Ancestry.com DNA, LLC* v. *DNA Genotek Inc., Inter Partes* Review No. IPR2016-00060, Feb. 2, 2016, 6 pages.
Petitioner Ancestry.com DNA, LLC's Motion for Pro Hac Vice Admission of Melanie L. Mayer Pursuant to 37 C.F.R. § 42.10(c), *Ancestry.com DNA, LLC* v. *DNA Genotek Inc., Inter Partes* Review No. IPR2016-00060, Feb. 2, 2016, 7 pages.

Order Granting Motion to Expunge 37 C.F.R. § 42.7, *Ancestry.com DNA, LLC* v. *DNA Genotek Inc.*, Case IPR2016-00060, Jan. 6, 2016, 3 pages.
Petitioner's Certification of Subsitute Exhibit 1011, *Ancestry.com DNA, LLC* v. *DNA Genotek Inc., Inter Partes* Review No. IPR2016-00060, Dec. 15, 2015, 2 pages.
Petitioner's Motion to Expunge Previously Filed Exhibit 1011, *Ancestry.com DNA, LLC* v. *DNA Genotek Inc., Inter Partes* Review No. IPR2016-00060, Dec. 15, 2015, 4 pages.
Order Conduct of the Proceeding, 37 C.F.R. § 42.5, *Ancestry.com DNA, LLC* v. *DNA Genotek Inc.*, Case IPR2016-00060, Dec. 15, 2015, 3 pages.
Patent Owner's Mandatory Notices, *Ancestry.com DNA, LLC* v. *DNA Genotek Inc., Inter Partes* Review No. IPR2016-00060, Nov. 20, 2015, 6 pages.
Patent Owner's Power of Attorney Under 37 C.F.R. § 42.10(b), *Ancestry.com DNA, LLC* v. *DNA Genotek Inc., Inter Partes* Review No. IPR2016-00060, Nov. 19, 2015. 2 pages.
Resubmitted Petition for Inter Partes Review of U.S. Pat. No. 8,221,381, *Ancestry.com DNA, LLC* v. *DNA Genotek Inc., Inter Partes* Review No. IPR2016-00060, Nov. 5, 2015, 69 pages.
Notice of Filing Date Accorded to Petition and Time for Filing Patent Owner Preliminary Response, *Ancestry.com DNA, LLC* v. *DNA Genotek Inc.*, Case IPR 2016-00060, Nov. 3, 2016, 3 pages.
Petitioner Ancestry.com DNA LLC's Power of Attorney Pursuant to 37 C.F.R. § 42.10(b), *Ancestry.com DNA, LLC* v. *DNA Genotek Inc., Inter Partes* Review No. Unassigned, Oct. 17, 2015, 2 pages.
Petition for *Inter Partes* Review of U.S. Pat. No. 8,221,381, *Ancestry.com DNA, LLC* v. *DNA Genotek Inc., Inter Partes* Review No. Unassigned, Oct. 20, 2015, 69 pages.
Biomek FX User's Manual, May 2000, 6 pages.
Exhibits 1-11 for Collins Deposition, Case 1:15-cv-00661-SLR, Filed Nov. 5, 2015, 111 pages.
Declaration of John M. Collins in Support of DNA Genotek's Reply in Support of the Motion for Preliminary Injunction, *DNA Genotek Inc.* v. *Spectrum DNA; Spectrum Solutions L.L.C.;* and *Spectrum Packaging L.L.C.*, C.A. No. 15-cv-00661-SLR, Nov. 5, 2015, 43 pages.
Errata Sheet for the Deposition Transcript of John M. Colins, Ph.D., *DNA Genotek Inc.* v. *Spectrum DNA, et al.*, Case No. 15-cv-00661-SLR, Nov. 13, 2015, 2 pages.
Deposition of: John Collins, Ph.D., *DNA Genotek Inc.* vs. *Spectrum DNA, Spectrum Solutions L.L.C.*, and *Spectrum Packaging L.L.C.*, C.A. No. 15-CV-00661-SLR, Nov. 13, 2015, 148 pages.
Deposition of Terry Layton, Ph.D., *Ancestry.com DNA, LLC* vs. *DNA Genotek Inc.*, U.S. Pat. No. 8,221,381, *Inter Partes* Review No. 2016-00060, May 25, 2016, 172 pages.
Declaration of John M. Collins, Ph.D., *Ancestry.com DNA, LLC* v. *DNA Genotek, Inc., Inter Partes* Review No. IPR2016-00060, Jun. 22, 2016, 18 pages.
Declaration of Terry N. Layton, Ph.D., Ancestry.com DNA LLC, Inter Partes Review of U.S. Pat. No. 8,221,381, Oct. 20, 2015, 130 pages.
Declaration of Juan C. Lasheras, Ph.D., *DNA Genotek Inc.* v. *Spectrum DNA; Spectrum Solutions L.L.C.;* and *Spectrum Packaging L.L.C.*, C.A. No. 15-cv-00661-SLR, Aug. 24, 2015, 154 pages.
Biomek FX User's Manual, May 2000, 634 pages.
Holman, J.W. et al., "Evaluation of an Automated Preanalytical Robotic Workstation at Two Academic Health Centers," Clinical Chemistry, 2002, pp. 540-548, vol. 48, No. 3.
Errata Sheet for the Deposition Transcript of Juan Carlos Lasheras, Ph.D., *DNA Genotek Inc.* v. *Spectrum DNA et al.*, Case No. 15-cv-00661-SLR, Sep. 24, 2015, 4 pages.
Videotaped Deposition of Juan Carlos Lasheras, Ph.D., *DNA Genotek Inc.* v. *Spectrum DNA, Spectrum Solutions L.L.C.*, and *Spectrum Packaging L.L.C.*, C.A. No. 15-CV-00661-SLR, Sep. 24, 2015, 216 pages.
Resubmitted Petition for Inter Partes Review of U.S. Pat. No. 8,221,381, *Ancestry.com DNA, LLC* v. *DNA Genotek Inc., Inter Partes* Review No. IPR2016-00060, Nov. 5, 2015 (Resubmitted; originally filed Oct. 20, 2015), 69 pages.

(56) References Cited

OTHER PUBLICATIONS

U.S. District Court, District of Delaware (Wilmington) Civil Docket for Case #: 1:15-cv-00355-SLR-SRF, Date Filed May 4, 2015, 10 pages.
U.S. District Court, District of Delaware (Wilmington) Civil Docket for Case #: 1:15-cv-00661-SLR, Date Filed Jul. 31, 2015, 16 pages.
Prior Art Search for U.S. Pat. No. 8,221,381, GreyB Services Pte. Ltd., Dec. 16, 2015, 11 pages.
United States Decision on Appeal, U.S. Appl. No. 11/817,217, Sep. 30, 2014, 5 pages.
Tokai Corp. v. Easton Enterprises, Inc., 632 F.3d 1358 (2011), 23 pages.
Tec Air, Inc. v. Denso Mfg. Michigan Inc., 192 F.3d 1353 (1999), 10 pages.
Decision Request for Rehearing 37 C.F.R. § 42.71(d), *SAP America, Inc.* v. *Versata Development Group, Inc.*, CBM2012-00001, Sep. 13, 2013, 9 pages.
Riverbed Tech., Inc. v. Silver Peak Sys., 2013 U.S. Dist. LEXIS 102589, 7 pages.
Profectus Technology LLC v. Huawei Technologies Co., Ltd., 823 F.3d 1375 (2016), 11 pages.
Merck & Co., Inc. v. Teva Pharmaceuticals USA, Inc., 395 F. 3d 1364 (2005), 17 pages.
KSR Intern. Co. v. Teleflex Inc., 550 U.S. 398 (2007), 18 pages.
Application of Sponnoble, 56 C.C.P.A. 823 (1969), 12 pages.
In Re Robertson, 169 F. 3d 743 (1999), 6 pages.
In re Man Mach. Interface Techs. LLC, 822 F.3d 1282, 9 pages.
In re Gordon, 733 F. 2d 900 (1984), 5 pages.
In re Gianelli, 736 F.3D 1375 (2014), 8 pages.
Ex Parte Masham, 2 U.S.P.Q.2d 1647 (1987), 3 pages.
Elekta Instrument S.A. v. O.U.R. Scientific Intern., Inc., 214 F.3d 1302 (2000), 9 pages.
Continental Can Co. USA, Inc. v. Monsanto Co., 948 F.2d 1264 (1991), 13 pages.
Aspex Eyewear, Inc. v. Marchon Eyewear, Inc., 672 F.3d 1335 (2012), 16 pages.
Petitioner's Trial Demonstratives, IPR2016-00060, U.S. Pat. No. 8,221,381, 65 pages.
Patent Owner's Demonstratives: Hearing for *Inter Partes* Review, *Ancestry.com DNA, Inc.* v. *DNA Genotek, Inc.*, Case No. IPR2016-00060, Dec. 6, 2016, 35 pages.
Patent Owner's Demonstratives as served: Hearing for *Inter Partes* Review, *Ancestry.com DNA, Inc.* v. *DNA Genotek, Inc.*, Case No. IPR2016-00060, Dec. 6, 2016, 35 pages.
Atlantic Research Marketing Systems, Inc. v. Troy, 659 F.3d 1345 (2011), 18 pages.
Graham v. John Deere Co. of Kansas City, 383 U.S. 1 (1966), 25 pages.
In re Kahn, 441 F.3d 977 (2006), 14 pages.
PPG Industries, Inc. v. Celanese Polymer Specialties Co., Inc., 840 F.2d 1565 (1988), 9 pages.
Renda Marine, Inc. v. U.S., 509 F.3d 1372 (2007), 9 pages.
Petition for Inter Partes Review of U.S. Pat. No. 8,221,381, *Ancestry.com DNA, LLC* v. *DNA Genotek Inc., Inter Partes* Review No. Unassigned, Jun. 3, 2016, 86 pages.
Notice of Filing Date Accorded to Petition and Time for Filing Patent Owner Preliminary Response, *Ancestry.com DNA, LLC* v. *DNA Genotek Inc.*, Case IPR2016-0115, Jun. 9, 2016, 5 pages.
Petitioner Ancestry.com DNA LLC's Power of Attorney Pursuant to 37 C.F.R. § 42.10 (b), *Ancestry.com DNA, LLC* v. *DNA Genotek Inc., Inter Partes* Review No. Unassigned, Oct. 17, 2015, 2 pages.
Patent Owner's Power of Attorney Under 37 C.F.R. § 42.10(b), *Ancestry.com DNA, LLC* v. *DNA Genotek Inc., Inter Partes* Review IPR2016-01152, Jun. 23, 2016, 2 pages.
Patent Owner's Mandatory Notices, *Ancestry.com DNA, LLC* v. *DNA Genotek Inc., Inter Partes* Review No. IPR2016-01152, Jun. 24, 2016, 6 pages.
Patent Owner's Preliminary Response, *Ancestry.com DNA, LLC* v. *DNA Genotek Inc., Inter Partes* Review No. IPR2016-01152, Sep. 9, 2016, 50 pages.
Petitioner Ancestry.com DNA, LLC's Motion for Pro Hac Vice Admission of Michael J. Sacksteder Pursuant to 37 C.F.R. § 42.10 (c), *Ancestry.com DNA, LLC* v. *DNA Genotek Inc., Inter Partes* Review No. IPR 2016-01152, Sep. 20, 2016, 7 pages.
Petitioner Ancestry.com DNA, LLC's Motion for Pro Hac Vice Admission of Melanie L. Mayer Pursuant to 37 C.F.R. § 42.10 (c), *Ancestry.com DNA, LLC* v. *DNA Genotek Inc., Inter Partes* Review No. IPR2016-01152, Sep. 20, 2016, 7 pages.
Order Granting Motion for Pro Hac Vice Admission of Melanie L. Mayer 37 C.F.R. § 42.10, *Ancestry.com DNA, LLC* v. *DNA Genotek Inc.*, Case IPR2016-01152, Sep. 28, 2016, 3 pages.
Order Granting Motion for Pro Hac Vice Admission of Michel J. Sacksteder 37 C.F.R. § 42.10, *Ancestry.com DNA, LLC* v. *DNA Genotek Inc.*, Case IPR2016-01152, Sep. 28, 2016, 3 pages.
Decision Denying Institution of Inter Partes Review 37 C.F.R. § 42.108, *Ancestry.com DNA, LLC* v. *DNA Genotek Inc.*, Case IPR2016-01152, Nov. 23, 2016, 13 pages.
Petitioner Ancestry.com DNA LLC's Request for Rehearing and Reconsideration Under 37 C.F.R. § 42.71(d), *Ancestry.com DNA, LLC* v. *DNA Genotek Inc., Inter Partes* Review No. IPR2016-01152, Dec. 23, 2016, 19 pages.
Petition for Inter Partes Review of U.S. Pat. No. 6,974,569 Under 35 U.S.C. §§ 311-319 and 37 C.F.R. §§ 42.1-.80, 42.100-.123, *Conopco, Inc. dba Unilever* v. *The Procter & Gamble Company*, Case IPR: Unassigned, Aug. 14, 2013, 64 pages.
Petition for Inter Partes Review of U.S. Pat. No. 6,974,569 Under 35 U.S.C. §§ 311-319 and 37 C.F.R. §§ 42.1-.80, 42.100-.123, *Conopco, Inc. dba Unilever* v. *The Procter & Gamble Company*, Case IPR: Unassigned, Mar. 12, 2014, 62 pages.
U.S. Pat. No. 8,221,381 File History, Filed Nov. 24, 2008, 401 pages.
Plaintiff DNA Genotek Inc.'s Opening Brief in Support of Motion for Preliminary Injunction, Jury Trial Demanded, *DNA Genotek Inc.* v. *Spectrum DNA; Spectrum Solutions L.L.C.;* and *Spectrum Packaging, L.L.C.*, C.A. No. 15-cv-00661-SLR, Aug. 24, 2015, 26 pages.
Defendants' Brief in Opposition to DNA Genotek's Motion for Preliminary Injunction, *DNA Genotek Inc.* v. *Spectrum DNA; Spectrum Solutions L.L.C.;* and *Spectrum Packaging, L.L.C.*, C.A. No. 15-661-SLR, Oct. 9, 2015, 37 pages.
Declaration of Terry Layton, Ph.D. In Support of Defendants' Opposition to DNA Genotek's Motion for Preliminary Injunction, *DNA Genotek Inc.* v. *Spectrum DNA; Spectrum Solutions L.L.C.;* and *Spectrum Packaging, L.L.C.*, C.A. No. 15-cv-00661-SLR, Oct. 2, 2015, 38 pages.
U.S. Appl. No. 60/523,104, filed Nov. 19, 2003, 8 pages.
'381 Claim Element or Limitation Chart, undated, 4 pages.
Summons in a Civil Action, *DNA Genotek Inc.* v. *Ancestry.com DNA, LLC*, Civil Action No. 15-355, May 5, 2015, 2 pages.
Response to the Notice of Non-Compliant Appeal Brief, U.S. Appl. No. 12/338,873, Oct. 24, 2014, 4 pages.
Patent Assignment Abstract of Title, U.S. Appl. No. 12/338,873, Jun. 1, 2016, 1 page.
Deposition of: John Collins, Ph.D., *DNA Genotek Inc.* v. *Spectrum DNA; Spectrum Solutions L.L.C.;* and *Spectrum Packaging, L.L.C.*, C.A. No. 15-CV-00661-SLR, Nov. 13, 2015, 3 pages.
Declaration of Michael J. Sacksteder in Support of Petitioner's Motion for Pro Hac Vice Admission of Michael J. Sacksteder Pursuant to 37 C.F.R. § 42.10 (c), *Ancestry.com DNA, LLC* v. *DNA Genotek Inc., Inter Partes* Review No. IPR2016-01152, Sep. 20, 2016, 3 pages.
Declaration of Melanie L. Mayer in Support of Petitioner's Motion for Pro Hac Vice Admission of Melanie L. Mayer Pursuant to 37 C.F.R. § 42.10 (c), *Ancestry.com DNA, LLC* v. *DNA Genotek Inc., Inter Partes* Review No. IPR2016-01152, Sep. 20, 2016, 4 pages.
Petitioner Ancestry.com DNA, LLC's Power of Attorney Pursuant to 37 C.F.R. § 42.10(b), U.S. Pat. No. 9,207,164, *Ancestry.com DNA, LLC* v. *DNA Genotek Inc., Inter Partes* Review No. Unassigned, Oct. 17, 2015, 2 pages.
Petition for *Inter Partes* Review of U.S. Pat. No. 9,207,164, *Ancestry.com DNA, LLC* v. *DNA Genotek Inc., Inter Partes* Review No. Unassigned, Jul. 20, 2016, 83 pages.

(56) References Cited

OTHER PUBLICATIONS

Patent Owner's Mandatory Notices, *Ancestry.com DNA, LLC* v. *DNA Genotek Inc., Inter Partes* Review No. IPR2016-01467, Aug. 12, 2016, 6 pages.
Notice of Filing Date Accorded to Petition and Time for Filing Patent Owner Preliminary Response, *Ancestry.com DNA, LLC* v. *DNA Genotek Inc.*, Case IPR2016-01467, Aug. 17, 2016, 5 pages.
Patent Owner's Power of Attorney Under 37 C.F.R. § 42,10(b), *Ancestry.com DNA, LLC* v. *DNA Genotek Inc., Inter Partes* Review No. IPR2016-01467, Aug. 4, 2016, 2 pages.
Petitioner Ancestry.com DNA, LLC's Motion for Pro Hac Vice Admission of Michael J. Sacksteder Pursuant to 37 C.F.R. § 42.10(c), *Ancestry.com DNA, LLC* v. *DNA Genotek Inc., Inter Partes* Review No. IPR 2016-01467, Sep. 20, 2016, 7 pages.
Petitioner Ancestry.com DNA, LLC's Motion for Pro Hac Vice Admission of Melanie L. Mayer Pursuant to 37 C.F.R. § 42.10(c), *Ancestry.com DNA, LLC* v. *DNA Genotek Inc., Inter Partes* Review No. IPR 2016-01467, Sep. 20, 2016, 7 pages.
Patent Owner's Preliminary Response, *Ancestry.com DNA, LLC* v. *DNA Genotek Inc., Inter Partes* Review No. IPR2016-01467, Nov. 17, 2016, 53 pages.
Decision Institution of Inter Partes Review 37 C.F.R. § 42.108, *Ancestry.com DNA, LLC* v. *DNA Genotek Inc.*, Case IPR2016-00060, 23 pages.
Defendant's Responsive Claim Construction Brief, *DNA Genotek Inc.* v. *Ancestry.com DNA, LLC*, C.A. No. 15-355-SLR-SRF, Oct. 21, 2016, 36 pages.
U.S. File History, U.S. Pat. No. 9,207,164, Filed Jun. 28, 2012, 545 pages.
Declaration of Terry N. Layton, Ph.D., Ancestry.com DNA, LLC, Inter Partes Review of U.S. Pat. No. 9,207,164, Jul. 250, 2016, 100 pages.
Affidavit of Service, *DNA Genotek Inc.* v. *Spectrum Solutions L.L.C.; Spectrum DNA*, Case No. 16-cv-01544-JLS-NLS, Jun. 23, 2016, 2 pages.
Chart Comparison of '164 and '381 Claim Limitations, Jul. 21, 2016, 12 pages.
Memorandum of Points and Authorities in Support of Motion for Preliminary Injunction, *DNA Genotek Inc.* v. *Spectrum Solutions L.L.C.* and *Spectrum DNA*, Case No. 3:16-cv-01544-JLS-NLS, Jun. 21, 2016, 31 pages.
Declaration of Juan C. Lasheras, PH.D., in Support of Motion for Preliminary Injunction, *DNA Genotek Inc.* v. *Spectrum Solutions L.L.C.* and *Spectrum DNA*, Case No. 16-cv-01544-JLS-NLS, Jun. 21, 2016, 27 pages.
Declaration of Michael J. Sacksteder in Support of Petitioner's Motion for Pro Hac Vice Admission of Michael J. Sacksteder Pursuant to 37 C.F.R. § 42.10(c), *Ancestry.com DNA, LLC* v. *DNA Genotek Inc., Inter Partes* Review No. IPR 2016-01467, Sep. 20, 2016, 4 pages.
Declaration of Melanie L. Mayer in Support of Petitioner's Motion for Pro Hac Vice Admission of Melanie L. Mayer Pursuant to 37 C.F.R. § 42.10(c), *Ancestry.com DNA, LLC* v. *DNA Genotek Inc., Inter Partes* Review No. IPR2016-01467, Sep. 20, 2016, 5 pages.
European Extended Search Report, European Application No. 14832139.1, dated Feb. 22, 2017, 8 pages.

\* cited by examiner

SAMPLE COLLECTION DEVICE

CROSS REFERENCE TO RELATED APPLICATIONS

This application claims the benefit of U.S. Provisional Application No. 61/861,329, filed Aug. 1, 2013, which is hereby incorporated in its entirety by reference.

REFERENCE TO A SEQUENCE LISTING

Not applicable.

STATEMENT REGARDING FEDERALLY SPONSORED RESEARCH OR DEVELOPMENT

Not applicable.

BACKGROUND OF THE INVENTION

The invention relates to sample collection devices useful for, e.g., collection of human saliva for DNA analysis.

There is a need for patient friendly devices to collect samples, e.g., human saliva, for nucleic acid analysis, e.g., analysis of DNA for the purposes of genealogy, personalized medicine, forensics, and the like. Optionally the sample collection device can be used at home without clinician supervision. A sample collection device typically includes a container for holding the sample, e.g., a tube; a means for directing saliva into the tube, e.g., a funnel; a closure for the tube, e.g., a cap; and a composition for stabilization of the sample during transport from the patient's location, e.g., the patient's home, to the analysis location.

Current sample collection devices can be difficult to use. Difficulties include awkward sizes for a typical hand; unwieldy numbers of steps for use; unclear indications of orientation of tube; instability on flat surface; caps resistant to closure; inconsistent combining of sample with stabilization composition; and non-fail safe methods for connecting a patient record to a sample record.

Examples of devices and compositions can be found in the following patents and published patent applications: WO 2003104251 A9; US20120061392; US20100099149; US20110212002; and U.S. Pat. No. 7,482,116

BRIEF DESCRIPTION OF THE SEVERAL VIEWS OF THE DRAWINGS

These and other features, aspects, and advantages of the present invention will become better understood with regard to the following description, and accompanying drawings, where:

FIG. 1A illustrates each component of the invention: a sample tube with a plug; a funnel; and a cap with capsule, seal, and piercing insert. FIG. 1B illustrates a sample tube connected to a cap. FIG. 1C illustrates a sample tube connected to a funnel.

DETAILED DESCRIPTION OF THE INVENTION

Briefly, and as described in more detail below, described herein is a sample collection device having a sample tube, a funnel connectable to the tube, and a cap connectable to the tube, the cap having a sealed capsule and a piercing device. The capsule optionally includes a stabilization fluid for nucleic acid (e.g., DNA) stabilization during transport and storage.

The invention is useful for collection of a human saliva sample, transportation of the sample to an analysis location, and storage of the sample. In some embodiments, the invention is useful for in-home collection by the patient.

Advantages of this sample collection device are numerous. The device can be used without clinician supervision. The design results in an easy-to-use method for sample collection. The presence of the funnel on the sample tube upon arrival at the user's location identifies the correct end of the sample tube for receiving the sample. The plug on one end of the tube stabilizes the tube when placed on a flat surface. Removal of the funnel and closing the tube with the cap are performed with simple motions. The piercing insert ensures that the seal is irreversibly opened once the cap is screwed onto the tube, and facilitates complete mixing of the stabilization fluid in the capsule and the sample in the tube.

Figure 1:
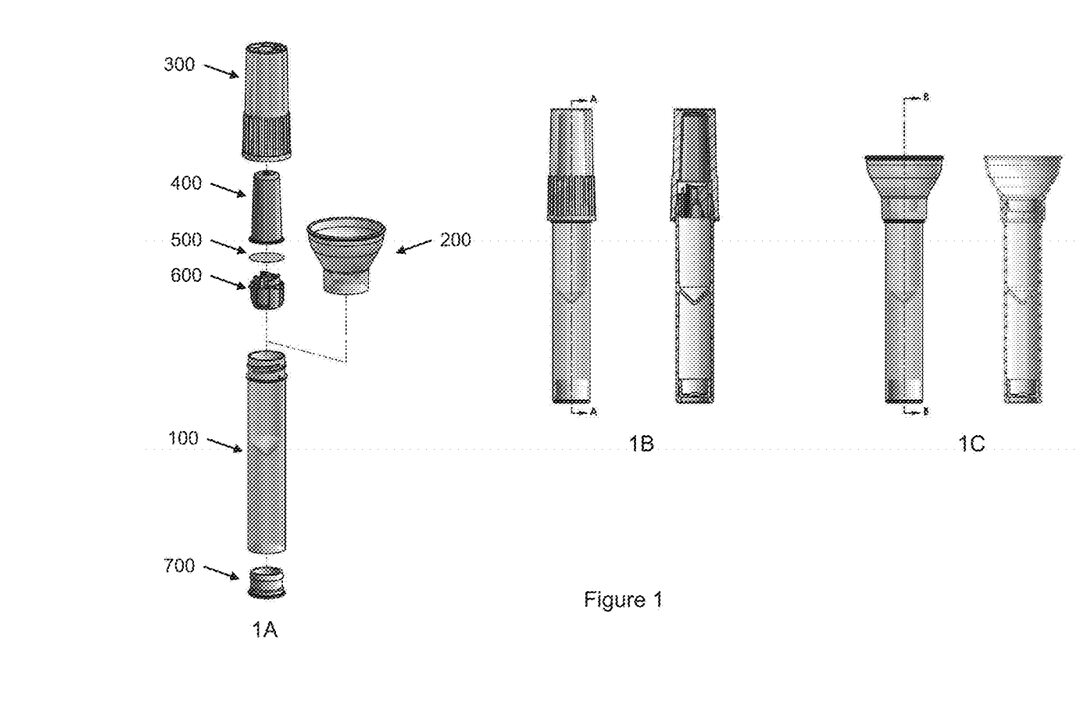
FIG. 1 depicts a sample collection device of the invention.

Turning to FIG. 1, FIG. 1A illustrates one embodiment of the invention. The sample collection device includes a sample collection tube 100, a connectable funnel 200, and connectable cap 300. The cap encloses a capsule 400 closed with a pierceable seal 500, and a piercing insert 600. One end of the sample tube includes a removable plug 700. The sealed capsule can contain a stabilization fluid.

In one embodiment, the device is provided to the user with the funnel connected to the sample tube as shown in FIG. 1C. As described in more detail below, the funnel connects to the tube via flanges.

As shown in FIG. 1B, the funnel can be removed (e.g., after the sample has been placed in the tube) and the cap, containing the sealed capsule and the piercing device, can be screwed onto the tube via threads on the outside of the tube and on the inside of the cap. Once the cap is fully screwed onto the tube, the piercing device is moved towards the capsule and contacts the seal. The seal is pierced resulting in the flow of the stabilization fluid from the capsule into the tube to be mixed with the sample.

Figure 2:
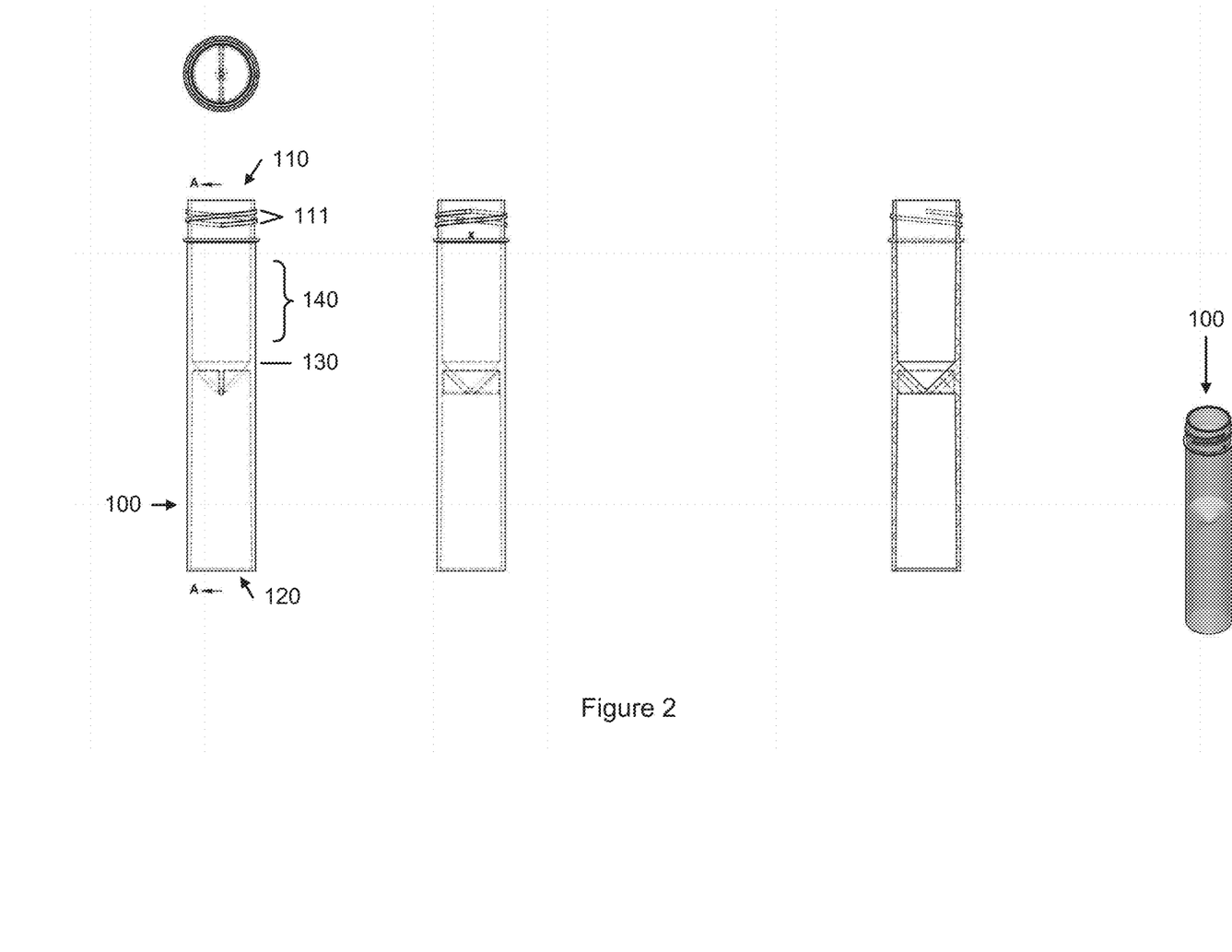
FIG. 2 depicts a sample tube.

FIG. 2 illustrates the sample tube 100. The sample tube includes a first opened end 110 and a second opened end 120. The second opened end is typically closed with a removable plug. The first opened end is connectable to either the funnel via flanges on the funnel or the cap via threads 111 on the outside wall of the tube. The sample tube includes a dividing member 130. This creates a sample collection portion of the tube, 140, that holds up to 2 milliliters of sample, e.g., saliva.

The full length of the tube leads to increased stability, ease of handling, and space for identification, e.g., labels and barcodes. The shorter sample collection portion reduces maximum sample size and increases efficiency of mixing of the sample and stabilization fluid.

Figure 3:
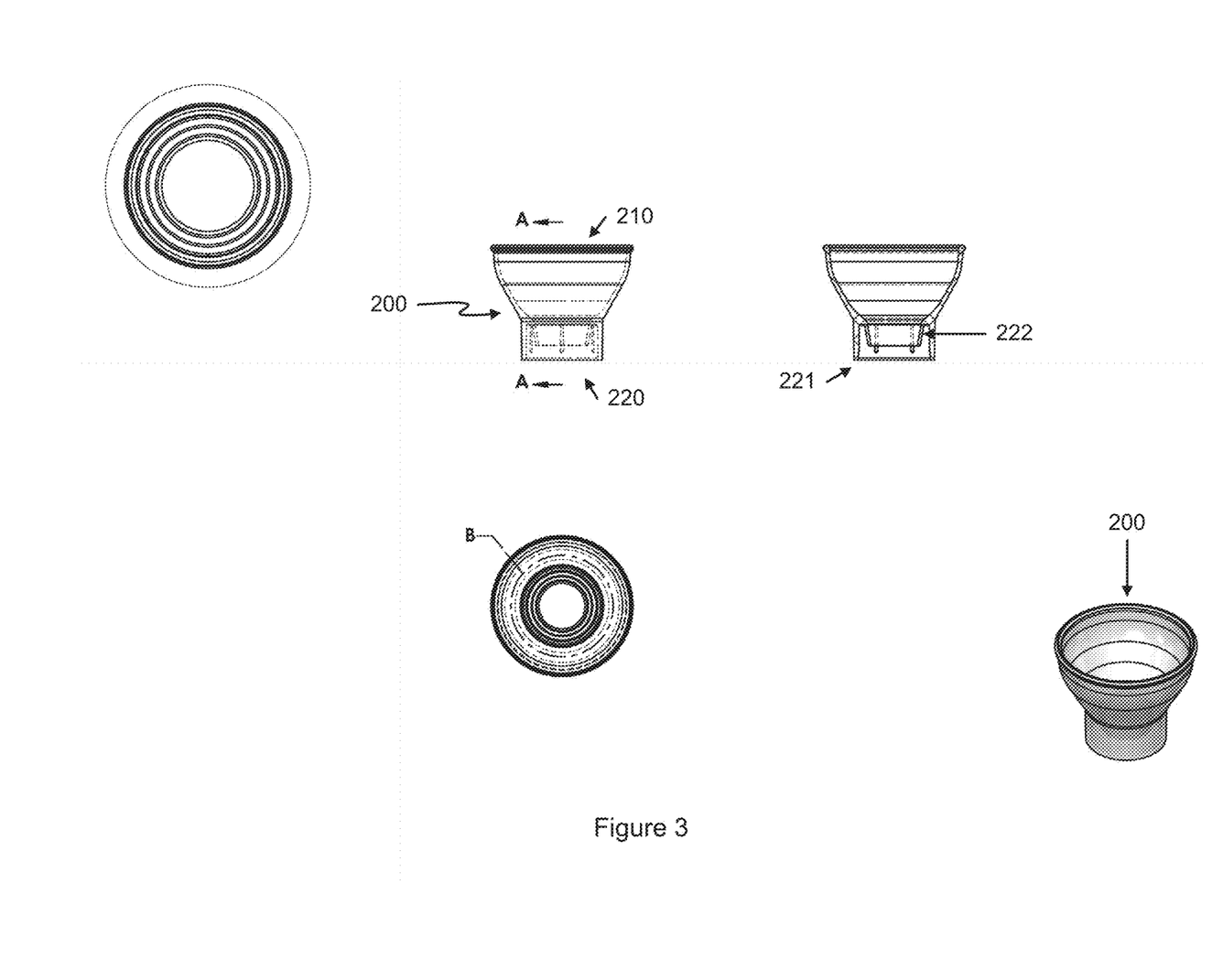
FIG. 3 depicts a funnel.
Figure 8:
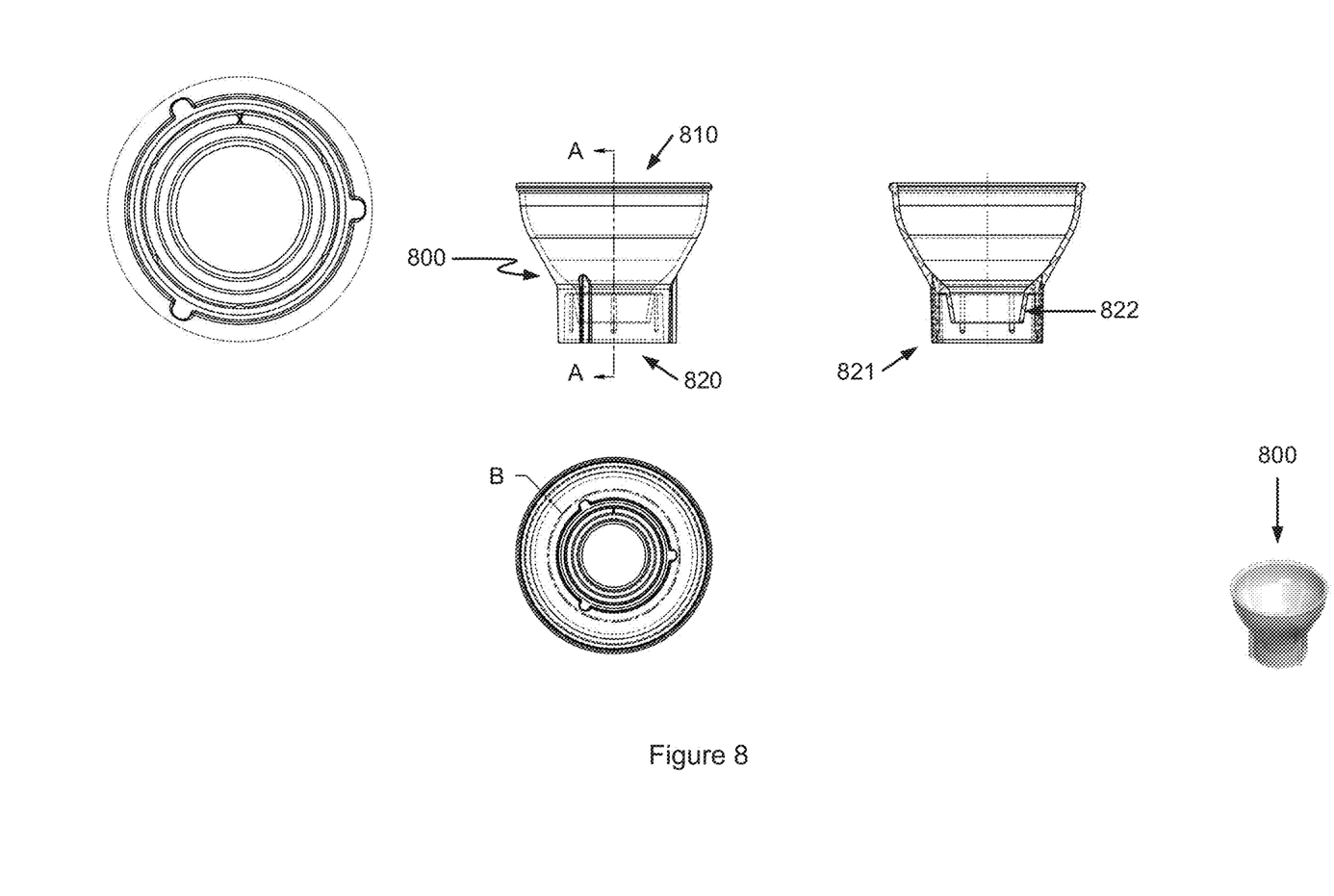
FIG. 8 depicts another embodiment of a funnel.

FIG. 3 illustrates the funnel 200. The funnel includes a larger first end 210 for receiving the sample, typically via expectorating by the user. The funnel includes a smaller second end 220 connectable to the first end of the sample tube. The second end has an outer wall 221 and an inner wall 222 creating flanges enclosing a space 223. The space 223 is of a size to snugly and reversibly insert the first end of the sample tube. In some embodiments the funnel of FIG. 8 is used.

Typically the sample collection device is delivered to the user with the funnel connected to the sample tube. This leaves no doubt as to which end of the tube receives the sample.

Figure 4:
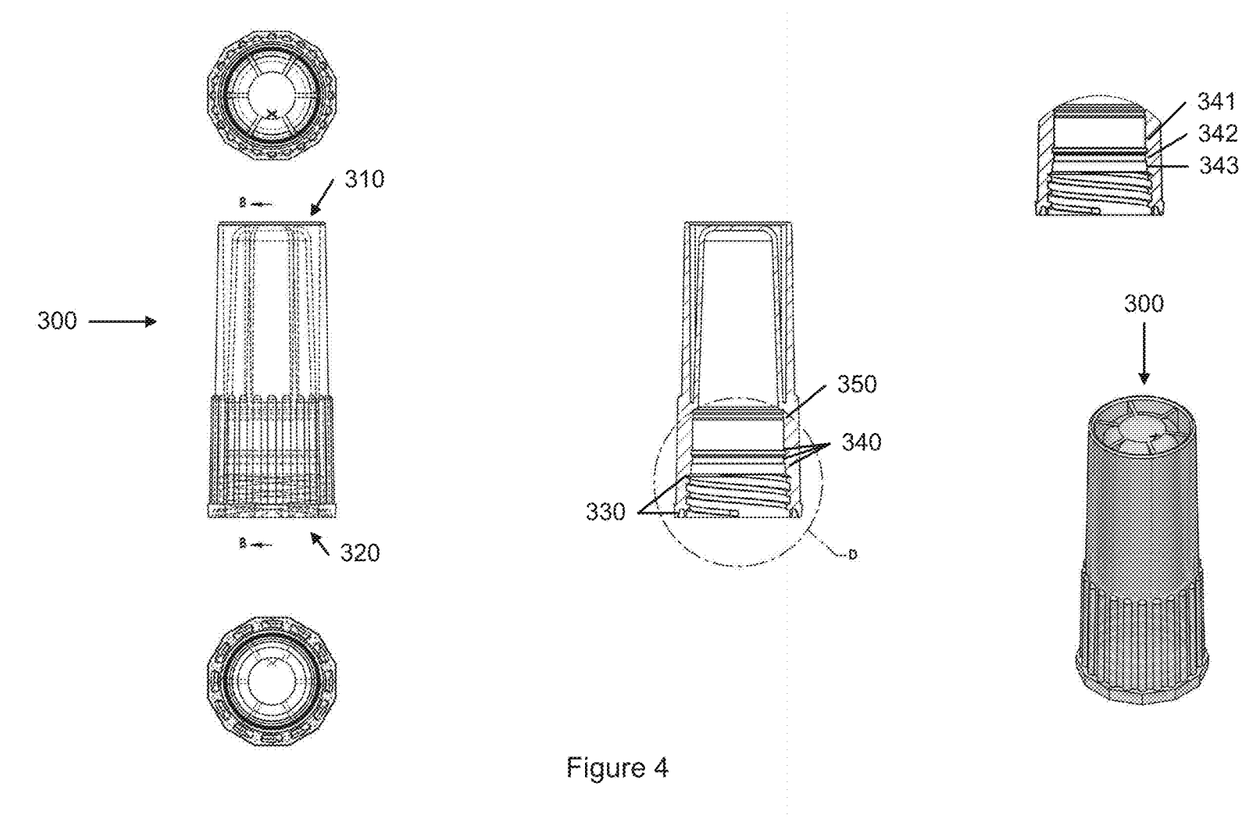
FIG. 4 depicts a cap.
Figure 9:
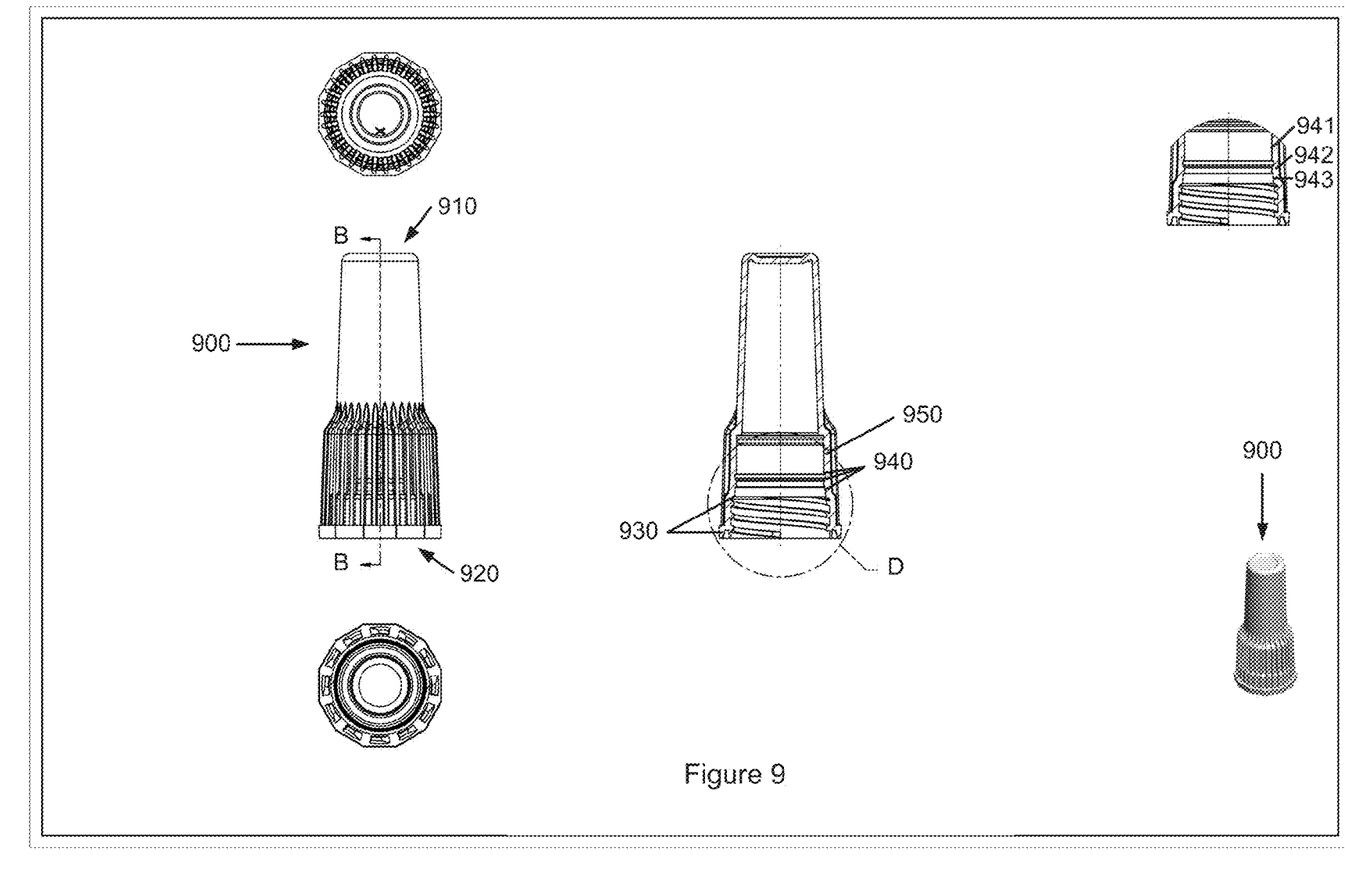
FIG. 9 depicts another embodiment of a cap.

FIG. 4 illustrates the cap 300. The cap includes a closed first end 310 and an open second end 320. The second cap end is configured to connect to the first end of the sample tube, e.g., via threads 330 on the inside of the cap near the second cap end. The cap is configured to hold the sealed capsule and the piercing insert. Grooves 340 on the inside of the cap assist in holding the piercing insert. In one embodiment the cap includes three grooves 341, 342, and 343. A ledge 350 on the inside of the cap presents a seat for the capsule once inserted. The grooves 340 are located between the threads 330 and the ledge 350. In some embodiments the cap of FIG. 9 is used.

Figure 5:
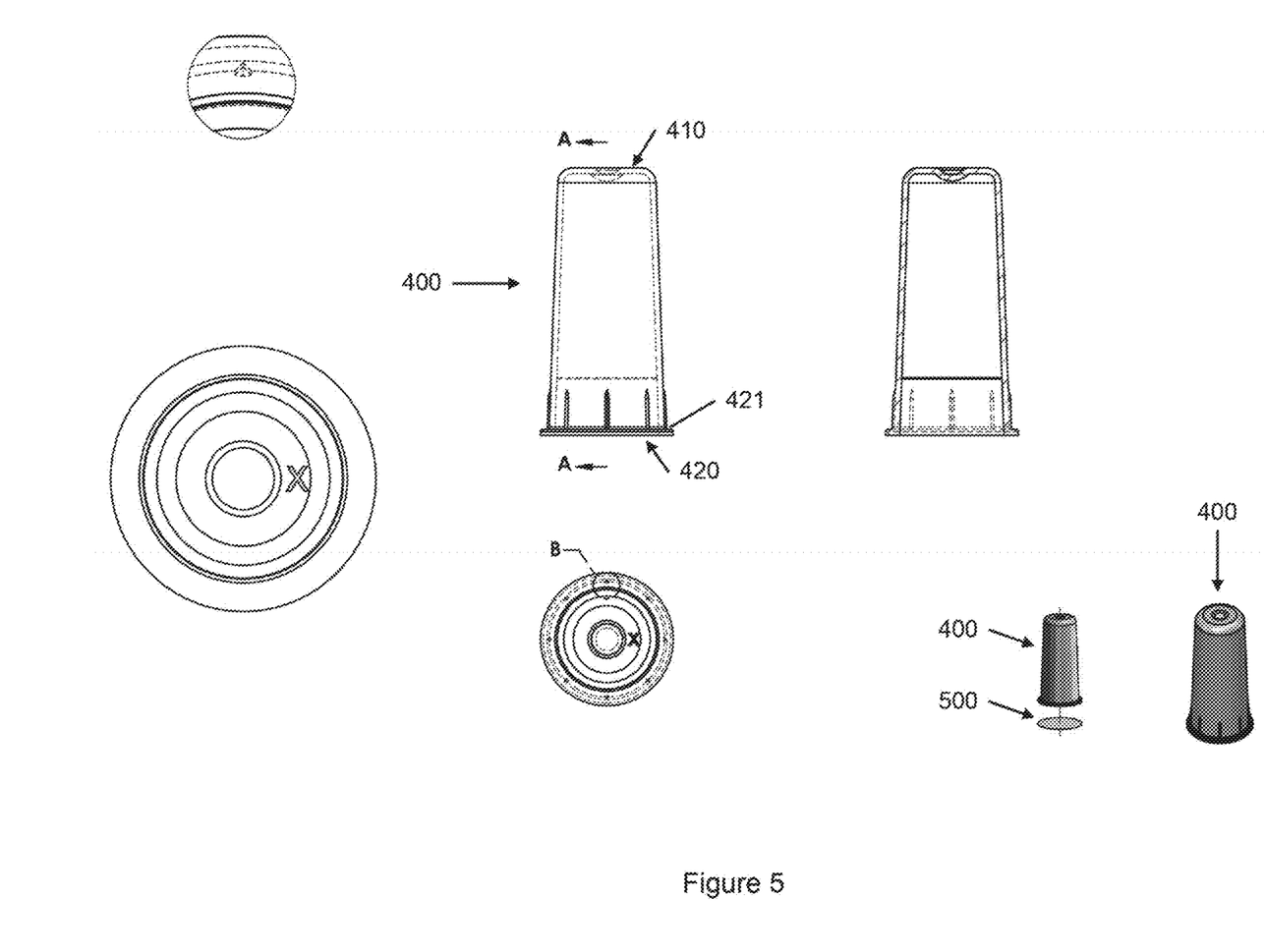
FIG. 5 depicts a capsule.

FIG. 5 illustrates the capsule 400. The capsule can include a stabilization fluid. The capsule 400 includes a closed first end 410 and an open second end 420. The second end 420 is sealed with a pierceable seal 500. The second end 420 includes an outer flange 421 surrounding the opening. The outer flange 421 rests on the ledge 350 when the capsule 400 in inserted into the cap 300.

The pierceable seal 500 closes the second end of the capsule 400. The seal is manufactured from, e.g., a metallic foil, e.g., an aluminum lidding foil. The foil can be 15-50 micrometers thick, e.g., 20 micrometers or 25 micrometers thick. The foil can include a heat seal lacquer material for pharmaceutical applications requiring a welded seal to polypropylene. Examples of materials for the seal include TEKNILID 1254 product and TEKNILID 1256 product (TEKNIPLEX, Tekini-Films USA, Somerville, N.J.). Properties of the seal include ability to withstand corrosion by the stabilization fluid, resistance to breakage during manufacture and transport to the user and before piercing by the piercing insert, and ease of piercing by the piercing insert upon contact with force.

The capsule 400 is typically includes a stabilization fluid for stabilizing sample nucleic acids, e.g., DNA, during transport and storage. In one embodiment the capsule can hold 0.75 ml of stabilization fluid. In some embodiments, the stabilization fluid includes the an alcohol, at least one detergent, a buffer, and at least one salt.

Figure 6:
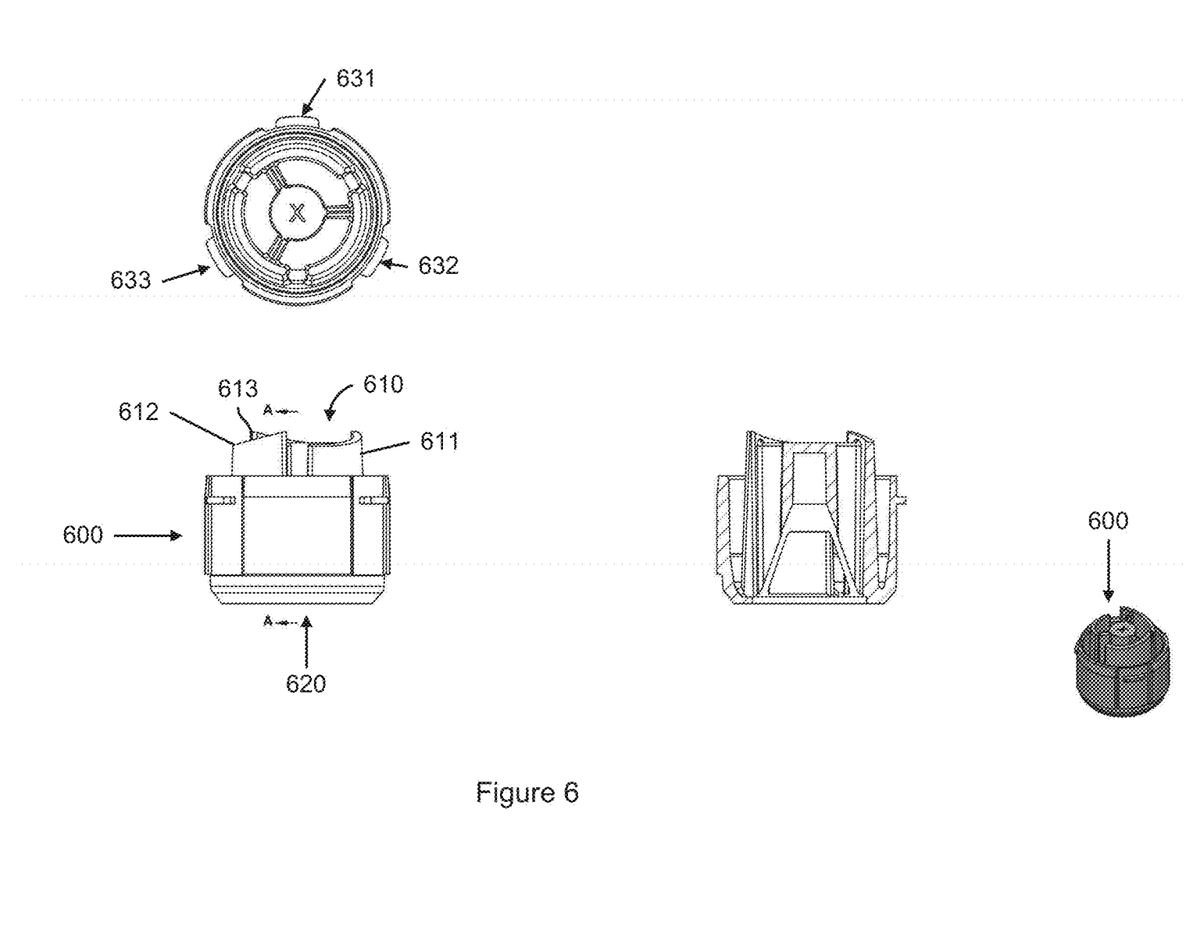
FIG. 6 depicts a piercing insert.
Figure 7:
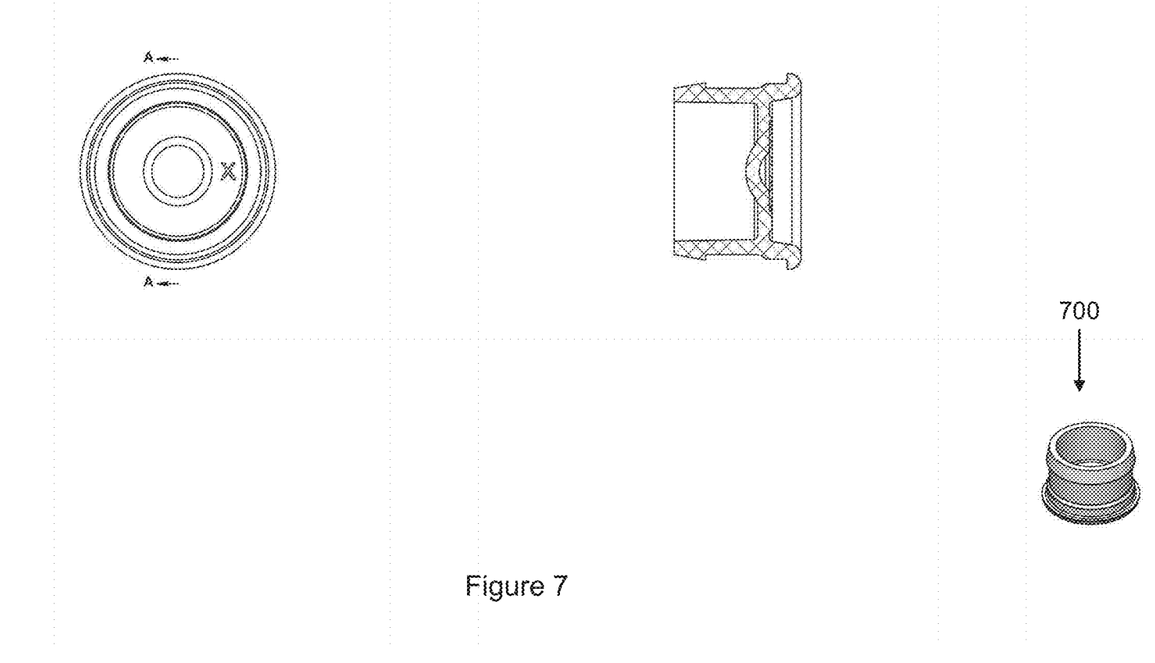
FIG. 7 depicts a plug 700.

FIG. 6 illustrates a piercing insert 600 which includes a first open end 610 with a piercing structures 611, 612, and 613 and a second open end 620. The piercing structures 611, 612, and 613 are configured to pierce the seal 500 once the cap is screwed onto the sample tube. The piercing structures 611, 612, and 613 are configured to prevent the seal from re-closing after piercing. The piercing element 600 includes flanges 631, 632, and 633 on the outside wall. The flanges 631, 632, and 633 are configured to rest in the grooves 341, 342, and 343 on the inside of the cap, holding the piercing insert in the cap and at a distance from the seal until the cap is screwed on the tube. The second open end 620 is configured to be seated in the first open end of the sample tube when the cap is screwed onto the tube. The cap is configures to easily close the tube.

While the present teachings are described in conjunction with various embodiments, it is not intended that the present teachings be limited to such embodiments. On the contrary, the present teachings encompass various alternatives, modifications, and equivalents, as will be appreciated by those of skill in the art. Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

All references, issued patents and patent applications cited within the body of the instant specification are hereby incorporated by reference in their entirety, for all purposes.

What is claimed is:

1. A sample collection device comprising:
   a sample tube comprising:
      a first opened end; and
      a thread region near the first opened end;
   a funnel comprising:
      a first opened end for receiving a sample; and
      a second opened end, the first opened end being larger than the second opened end, the second opened end comprising an outer portion and an inner portion enclosing a space sufficiently shaped so as to be removably connectable to at least a portion of the first opened end of the sample tube;
   a cap comprising:
      a first closed end;
      a second opened end;
      a thread region near the second opened end configured to mate with the thread region of the sample tube, the cap removably connectable to the sample tube via their respective thread regions, the cap interchangeable with the funnel;
      a ledge formed on an interior surface of the cap; and
      at least one groove formed on the interior surface of cap, and
      the cap enclosing a capsule and a piercing insert;
   the capsule comprising:
      a first closed end; and
      a second opened end covered by a pierceable seal, the second opened end having a lip resting on the ledge in the cap, and
      the capsule configured to hold a stabilizing solution;
   the piercing insert comprising:
      a first opened end comprising at least one piercing protrusion;
      a second opened end;
      at least one channel extending between the first opened end and the second opened end; and
      at least one outer flange configured to mate with the at least one groove in the cap, and
      the at least one piercing protrusion, pierceable seal, and thread region of the cap arranged so that as the sample tube is removably connected to the cap via the thread regions of the cap and the sample tube, the at least one piercing protrusion pierces the seal.

2. The sample collection device of claim 1, wherein the sample tube is configured to hold 0.5 to 2.0 ml of the sample.

3. The sample collection device of claim 1, wherein the capsule further comprises the stabilizing solution.

4. The sample collection device of claim 1, wherein the capsule is configured to hold 0.75 ml of stabilizing solution.

5. The sample collection device of claim 1, wherein the pierceable seal comprises aluminum lidding foil.

6. The sample collection device of claim 1, wherein the pierceable seal comprises aluminum lidding foil and a heat based seal lacquer material.

7. The sample collection device of claim 1, wherein the sample tube, sample funnel, the cap, the piercing insert and the capsule comprise polypropylene 9074 (medium).

8. A kit comprising the sample collection device of claim 1 and instructions for use.

9. A method for collecting and stabilizing nucleic acids in a sample using the sample collection device of claim 1, comprising: connecting the second opened end of the funnel to the first opened end of the sample tube; collecting the sample through the first opened end of the funnel; allowing sample to flow through the funnel into the sample tube; removing the funnel; connecting the second opened end of the cap to the first opened end of the sample tube through their respective thread regions; twisting the cap relative to the sample tube; piercing the piercable seal with the at least one piercing protrusion on the piercing insert; allowing the stabilizing solution to flow through the at least one channel of the piercing insert into the sample tube; and shaking the sample collection device for at least 5 seconds, thereby mixing the stabilizing solution and the sample in the sample tube.

10. The method of claim 9, wherein the sample comprises human saliva collected via expectorating from the mouth.

11. The sample collection device of claim 1, wherein the sample tube further comprises:
a second opened end; and
a removable plug connected to the second opened end, and
wherein the sample tube is divided into a first portion and a second portion.

12. The sample collection device of claim 1, wherein the ledge formed on the interior surface of the cap is located proximal to the first closed end of the cap relative to the at least one groove, and wherein the at least one groove of the cap is located proximal to the second opened end relative to the ledge.

13. The sample collection device of claim 1, wherein a majority volume of the stabilizing solution is positioned between the first closed end of the cap and the ledge formed on the interior surface of the cap.

14. The sample collection device of claim 1, wherein the piercing insert is oriented within the cap such that the at least one protrusion is pointed towards the pierceable seal.

15. The sample collection device of claim 1, wherein the piercing insert is positioned proximal to the second opened end of the cap relative to the capsule.

* * * * *

UNITED STATES PATENT AND TRADEMARK OFFICE
CERTIFICATE OF CORRECTION

PATENT NO. : 9,732,376 B2  
APPLICATION NO. : 14/448721  
DATED : August 15, 2017  
INVENTOR(S) : Benjamin J. Oyler Page 1 of 1

It is certified that error appears in the above-identified patent and that said Letters Patent is hereby corrected as shown below:

In the Claims

Claim 1, Line 39: after "surface of" insert -- the --.

Signed and Sealed this
Twenty-ninth Day of May, 2018

Andrei Iancu
*Director of the United States Patent and Trademark Office*